United States Patent
Ademe

(10) Patent No.: US 9,766,114 B2
(45) Date of Patent: Sep. 19, 2017

(54) CAPSULE OBJECT INSPECTION SYSTEM AND ASSOCIATED METHOD

(71) Applicant: R.J. REYNOLDS TOBACCO COMPANY, Winston-Salem, NC (US)

(72) Inventor: Balager Ademe, Winston-Salem, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 104 days.

(21) Appl. No.: 14/835,962

(22) Filed: Aug. 26, 2015

(65) Prior Publication Data
US 2017/0059391 A1    Mar. 2, 2017

(51) Int. Cl.
| | |
|---|---|
| *G01G 19/00* | (2006.01) |
| *G01G 17/00* | (2006.01) |
| *B07C 5/342* | (2006.01) |
| *G01N 21/95* | (2006.01) |

(52) U.S. Cl.
CPC .............. *G01G 19/00* (2013.01); *B07C 5/342* (2013.01); *G01G 17/00* (2013.01); *G01N 21/9508* (2013.01)

(58) Field of Classification Search
CPC  G01D 21/02; G01D 5/58; G01D 5/54; G01D 5/26; G01G 19/00; G01G 17/00; G01B 9/00; G01B 9/02; G01B 9/0203; B07C 5/00; B07C 5/10; B07C 5/16; B07C 5/20; B07C 5/34; B07C 5/3404;
(Continued)

(56) References Cited

U.S. PATENT DOCUMENTS

| | | | | |
|---|---|---|---|---|
| 4,884,696 A | * | 12/1989 | Peleg | ........................ B07C 5/00 198/408 |
| 5,677,516 A | * | 10/1997 | Leverett | .................... B07C 5/18 177/145 |

(Continued)

OTHER PUBLICATIONS

"Keyence Gesamtkatalog Laser-Wegmessensoren", Jan. 1, 2010, XP050070040, Retrieved from the Internet: URL:http://www.keyence.de/dwn/lk_lj_general_kd.pdf [retrieved on Jul. 8, 2013].

*Primary Examiner* — Lisa Caputo
*Assistant Examiner* — Philip Cotey
(74) *Attorney, Agent, or Firm* — Womble Carlyle Sandridge & Rice LLP

(57) ABSTRACT

An inspection system configured to inspect a plurality of capsule objects is provided. The system includes an imaging device for capturing an image of the capsule object's exterior and a weighing device for measuring the capsule object's weight. The system also includes an analysis unit configured to analyze the captured images and the measured weights of the capsule objects. The analysis unit is configured to execute an edge detection tool that determines the capsule object's dimensions and whether the capsule object is defective based at least in part on the measured dimensions. The analysis unit is also configured to execute a weight analysis tool configured to determine whether the capsule object is defective based on the capsule object's weight. An associated method and a non-transitory, computer-readable storage medium having computer-readable program code portions stored therein that are executable by a processor are also provided.

20 Claims, 6 Drawing Sheets

(58) Field of Classification Search
CPC ......... B07C 5/342; B07C 5/3422; G07C 3/14;
G07C 3/143; G07C 3/146
USPC ........................................................ 73/865.8
See application file for complete search history.

(56) References Cited

U.S. PATENT DOCUMENTS

| | | | | |
|---|---|---|---|---|
| 5,917,927 | A * | 6/1999 | Satake | G06T 7/0004 356/237.1 |
| 6,026,686 | A * | 2/2000 | Hattori | G01N 29/045 702/56 |
| 6,407,807 | B1 | 6/2002 | Focke et al. | |
| 7,479,098 | B2 | 1/2009 | Thomas et al. | |
| 8,308,623 | B2 | 11/2012 | Nelson et al. | |
| 8,882,647 | B2 | 11/2014 | Thomas et al. | |
| 8,905,243 | B2 | 12/2014 | Dixon et al. | |
| 9,028,385 | B2 | 5/2015 | Thomas et al. | |
| 2001/0032807 | A1 * | 10/2001 | Powell, Jr. | B07C 5/18 209/592 |
| 2004/0128265 | A1 * | 7/2004 | Holtz | G06Q 10/08 705/406 |
| 2004/0151364 | A1 * | 8/2004 | Kenneway | B07C 5/3422 382/152 |
| 2004/0224020 | A1 | 11/2004 | Schoenhard | |
| 2005/0261864 | A1 * | 11/2005 | Edwards | G01B 11/00 702/127 |
| 2008/0253648 | A1 * | 10/2008 | Mulder | B07C 5/3422 382/165 |
| 2009/0306814 | A1 * | 12/2009 | Madden | B07C 5/342 700/223 |
| 2011/0067714 | A1 * | 3/2011 | Drewes | H04N 7/188 131/282 |
| 2011/0282488 | A1 * | 11/2011 | Horev | G06M 7/00 700/232 |
| 2012/0037546 | A1 * | 2/2012 | Dixon | B07B 13/10 209/640 |
| 2012/0085686 | A1 * | 4/2012 | Radema | B07C 5/3412 209/552 |
| 2013/0141115 | A1 | 6/2013 | Bourely et al. | |
| 2013/0144431 | A1 * | 6/2013 | Tidhar | B65B 5/103 700/231 |
| 2013/0235372 | A1 | 9/2013 | Voss | |
| 2013/0281277 | A1 | 10/2013 | Thomas et al. | |
| 2014/0052555 | A1 * | 2/2014 | MacIntosh | G06Q 20/208 705/23 |
| 2014/0104416 | A1 * | 4/2014 | Giordano | G01B 11/02 348/135 |
| 2014/0247339 | A1 * | 9/2014 | Brantley | A24C 5/3412 348/86 |
| 2014/0305850 | A1 * | 10/2014 | Serjeantson | B07C 3/08 209/546 |
| 2015/0047655 | A1 | 2/2015 | Thomas et al. | |

\* cited by examiner

CAPSULE OBJECT INSPECTION SYSTEM AND ASSOCIATED METHOD

FIELD OF THE DISCLOSURE

The present disclosure relates to capsule objects and more particularly to capsule object inspection systems and related methods. The capsule objects may be made or derived from tobacco, or otherwise incorporate tobacco, and may be intended for human consumption.

BACKGROUND OF THE DISCLOSURE

Popular tobacco products, such as cigarettes, smokeless tobacco products, and/or the like typically include a tobacco or tobacco-related material such as shredded tobacco (e.g., in cut filler form). Some tobacco products further include a capsule object within the tobacco and/or tobacco-related product. For example, smokeless tobacco products may include a pouch portion that includes a tobacco and/or tobacco-related material and a capsule therein. In another example, a cigarette may include a tobacco rod and a filter rod having a capsule included within the filter rod.

During the production of these tobacco products, inspection of the capsule and/or the tobacco product may occur. One example of a system for analyzing a tobacco product is set forth in U.S. Pat. App. Pub. No. 2014/0131579 to Ademe et al., which is incorporated herein by reference in its entirety. For example, inspection of the capsules to be included in the tobacco products may occur before, during, and/or after the production of the tobacco product. Inspection of the capsules during and/or after the production of the tobacco product that includes the capsule may provide additional difficulties. For example, a system configured to inspect capsules after the tobacco product has been produced could allow for the introduction of a defective capsule in the final tobacco product, thereby wasting materials by producing a defective tobacco product. In this regard, the manufactured tobacco product that includes the defective capsule cannot be sold for consumption because the perception of the quality of the product may be damaged.

As such, it may be desirable to inspect capsules to determine which capsules are defective before incorporating any capsules into a tobacco product. In particular, it may be desirable to determine if a capsule, which includes an outer shell and an inner payload, has dimensions, attributes, and/or properties that are substantially equal to or within predetermined acceptable interval limits. Further, it may be desirable to perform the inspection of capsules largely, or entirely, by high-speed automated machinery. As such, there exists a need for a system and method for inspecting capsules for defects prior to the capsules being included within a tobacco product for distribution and sale. It may also be desirable for such a solution to be readily implemented with respect to existing tobacco product production machinery.

SUMMARY OF THE DISCLOSURE

The above and other needs are met by aspects of the present disclosure which, in one aspect, provides a capsule object inspection system configured to inspect a plurality of capsule objects, each of the capsule objects including an outer shell and an inner payload. The system may include at least one imaging device configured to capture at least one image of the exterior of each of the capsule objects, a weighing device configured to measure the weight of each of the capsule objects, and an analysis unit configured to analyze the at least one image captured by the at least one imaging device and to analyze the weight measurement obtained by the weighing device for each of the capsule objects. The analysis unit may be configured to execute an edge detection tool configured to determine a dimension of each of the capsule objects based on the at least one captured image and to determine whether any of the capsule objects are defective based on the dimension. The analysis unit may be configured to execute a weight analysis tool configured to determine whether any of the capsule objects are defective based on the weight measurement.

In some embodiments, the inspection system may include a capsule dispensing device that includes a peripheral surface. The peripheral surface may define a plurality of cavities configured to receive the capsule objects therein. The capsule dispensing device may be configured to sequentially introduce the capsule objects to a detection zone, which may be defined by a field of view of the at least one imaging device. Additionally, the inspection system may include a capsule object repository that is operably engaged with the capsule dispensing device. According to some embodiments, the capsule object repository may be configured to retain a plurality of capsule objects therein.

According to another embodiment, the inspection system may include a weighing device that is configured to measure the weight of a series of capsule objects after the at least one imaging device has captured the at least one image of the at least one of the capsule objects. Additionally, the weighing device may be configured to recalibrate between measuring the weight of each capsule objects.

In some embodiments, the edge detection tool may be configured to determine a width of each of the capsule objects along a horizontal axis from the at least one image of the exterior of the capsule objects. In some embodiments, the edge detection tool may be configured to determine a height of the capsule objects along a vertical axis from the at least one image of the exterior of the capsule objects. In another embodiment, the analysis unit may be configured to execute a weight analysis tool that is configured to compare weight of each of the capsule objects with a predetermined capsule object weight interval.

Aspects of the present disclosure may also provide for a method for inspecting a plurality of capsule objects that include an outer shell and an inner payload. The method may include capturing one or more images of the capsule objects with at least one imaging device, determining a dimension of the capsule objects from the one or more images, weighing the capsule objects with a weighing device after the one or more images of the capsule objects are captured to determine a weight of each of the capsule objects, and determining whether the capsule objects are defective based on the weight and the dimension of the capsule objects. According to some embodiments, the method may include determining a width of the capsule objects along a horizontal axis of the capsule objects and a height of the capsule objects along a vertical axis of the capsule objects. The method may further include dispensing the capsule objects to a detection zone defined by a field of view of the at least one imaging device. In some embodiments, the method may include providing the capsule objects to a plurality of cavities defined by a peripheral surface of a dispensing device that is configured to sequentially dispense the capsule objects to the detection zone. According to some embodiments, the method may include dispensing the capsule objects to the weighing device. Additionally or alternatively, the method may include dropping the capsule objects from a dispensing device sequentially.

In some embodiments, the method may include weighing one of a series of capsule objects after the one or more images of the capsule objects are captured. The method may further include recalibrating the weighing device between weighing each of the capsule objects. In some embodiments, the method includes determining whether the capsule objects are defective. According to some embodiments, the method may include comparing the weight of the capsule objects with a predetermined capsule object weight interval. In some embodiments, the method may include comparing the dimension of the capsule objects with a predetermined capsule object dimension interval. According to another embodiment, the method may include discarding the capsule objects that are determined to be defective.

Aspects of the present disclosure may further provide a computer-readable storage medium that is non-transitory and has computer-readable program code portions stored therein. The computer-readable program code portions may, in response to execution by a processor, cause a system to at least capture at least one image of each of a plurality of capsule objects, determine a dimension of the capsule objects from the at least one image, measure a weight of each of the capsule objects, and determine whether each of the capsule objects is defective based on the at least one image and the weight.

According to some embodiments, the computer-readable program code portions, in response to execution by a processor, may cause a system to determine a width of each of the capsule objects along a horizontal axis of the capsule objects and a height of each of the capsule objects along a vertical axis of the capsule objects. In some embodiments, the computer-readable program portions, in response to execution by a processor, may cause the system to recalibrate a weighing device between measuring a weight of each of the capsule objects.

These and other features, aspects, and advantages of the disclosure will be apparent from a reading of the following detailed description together with the accompanying drawings, which are briefly described below.

BRIEF DESCRIPTION OF THE DRAWINGS

In order to assist the understanding of aspects of the disclosure, reference will now be made to the appended drawings, which are not necessarily drawn to scale and in which like reference numerals refer to like elements. The drawings are exemplary only, and should not be construed as limiting the disclosure.

DETAILED DESCRIPTION OF THE ASPECTS OF THE DISCLOSURE

The present disclosure will now be described more fully hereinafter with reference to exemplary aspects thereof. These exemplary aspects are described so that this disclosure will be thorough and complete, and will fully convey the scope of the disclosure to those skilled in the art. Indeed, the disclosure may be expressed in many different forms and should not be construed as limited to the aspects set forth herein; rather, these aspects are provided so that this disclosure will satisfy applicable legal requirements. As used in the specification, and in the appended claims, the singular forms "a", "an", "the", include plural referents unless the context clearly dictates otherwise.

Figure 1:
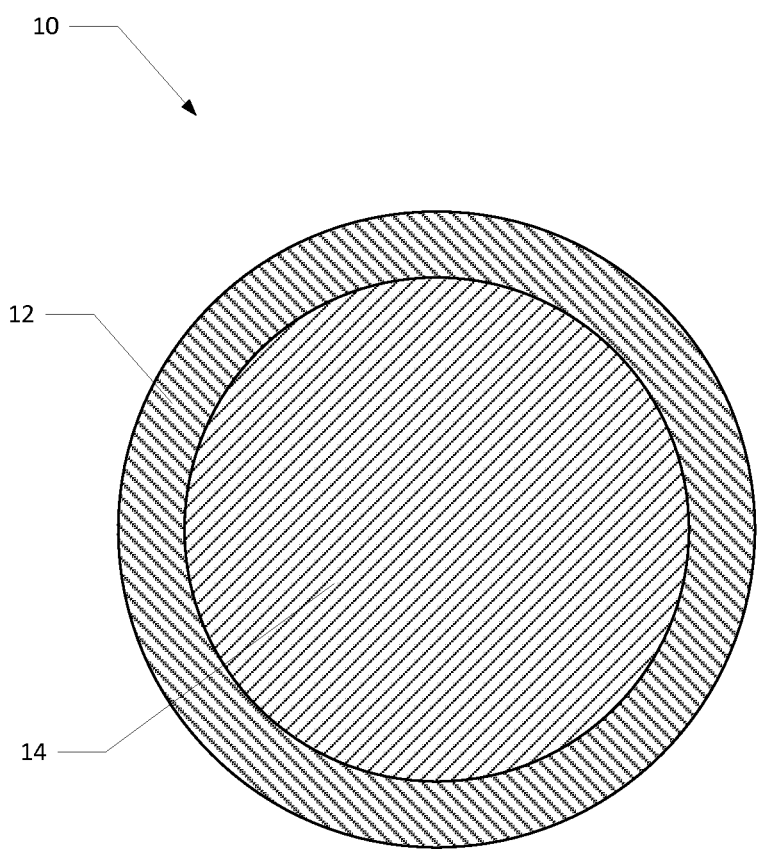
FIG. 1 illustrates a cross-sectional view through a capsule object according to an example aspect of the present disclosure.

As shown in FIG. 1, capsule objects 10 of the type disclosed herein may include an outer shell 12 incorporating an outer shell material, and an inner payload 14 incorporating an aqueous or non-aqueous liquid (e.g., a solution or dispersion of at least one flavoring ingredient within water or an organic liquid such as an alcohol or oil, or a mixture of water and a miscible liquid like alcohol or glycerin).

Representative types of capsules are of the type commercially available as "Momints" by Yosha! Enterprises, Inc. and "Ice Breakers Liquid Ice" from The Hershey Company. Representative types of capsules also have been incorporated in chewing gum, such as the type of gum marketed under the tradename "Cinnaburst" by Cadbury Adams USA. Representative types of capsules and components thereof also are set forth in U.S. Pat. No. 3,339,558 to Waterbury; U.S. Pat. No. 3,390,686 to Irby, Jr. et al.; U.S. Pat. No. 3,685,521 to Dock; U.S. Pat. No. 3,916,914 to Brooks et al.; U.S. Pat. No. 4,889,144 to Tateno et al. and U.S. Pat. No. 6,631,722 to MacAdam et al.; and PCT Application WO 03/009711 to Kim; which are incorporated herein by reference in their entireties. See also, the types of capsules and components thereof set forth in U.S. Pat. No. 5,223,185 to Takei et al.; U.S. Pat. No. 5,387,093 to Takei; U.S. Pat. No. 5,882,680 to Suzuki et al.; U.S. Pat. No. 6,719,933 to Nakamura et al.; U.S. Pat. No. 7,754,239 to Mane et al. and U.S. Pat. No. 6,949,256 to Fonkwe et al.; and U.S. Pat. App. Pub. Nos. 2004/0224020 to Schoenhard; 2005/0196437 to Bednarz et al. and 2005/0249676 to Scott et al.; which are incorporated herein by reference in their entireties.

Capsule objects 10 may be incorporated within tobacco products and/or tobacco-related products such as, for example, filter elements, rods of tobacco, and/or within smokeless tobacco products such as a snuff or snus product. In some aspects, the capsule object 10 may include an inner payload 14 that includes a flavoring agent configured to flavor the tobacco product. Examples of tobacco products including capsules are described in U.S. Pat. App. Pub. No. 2011/0271968 to Carpenter et al., U.S. Pat. No. 8,695,609 to Dube et al., U.S. Pat. No. 8,308,623 to Nelson et al., and U.S. Pat. No. 7,793,665 to Dube et al., each of which are incorporated herein by reference in their entireties.

Exemplary flavoring agents that can be encapsulated within the capsule objects 10 can be natural or synthetic, and the character of these flavors can be described, without limitation, as fresh, sweet, herbal, confectionary, floral, fruity or spice. Specific types of flavors include, but are not limited to, vanilla, coffee, chocolate, cream, mint, spearmint, menthol, peppermint, wintergreen, lavender, cardamom, nutmeg, cinnamon, clove, cascarilla, sandalwood, honey, jasmine, ginger, anise, sage, licorice, lemon, orange, apple, peach, lime, cherry, and strawberry. See also, Leffingwill et al., Tobacco Flavoring for Smoking Products, R. J. Reynolds Tobacco Company (1972). Flavorings also can include components that are considered moistening, cooling or smoothening agents, such as eucalyptus. These flavors may be provided neat (i.e., alone) or in a composite (e.g., spearmint and menthol, or orange and cinnamon). Composite flavors may be combined in a single capsule object 10 as a mixture, or as components of multiple capsule objects 10. Preferably, the capsule objects 10 do not incorporate any tobacco within their outer shells 12, or within their inner payload 14 regions. However, if desired, other embodiments of capsule objects may incorporate tobacco (e.g., as finely group tobacco pieces and/or tobacco extracts) within their outer shells and/or within their inner payload regions. See, for example, U.S. Pat. No. 7,836,895 to Dube et al., which is incorporated herein by reference in its entirety.

In some aspects, the inner payload 14 is a mixture of a flavoring agent and a diluting agent or carrier. A preferred diluting agent is a triglyceride, such as a medium chain triglyceride, and more particularly a food grade mixture of medium chain triglycerides. See, for example, Radzuan et al., Porim Bulletin, 39, 33-38 (1999). The amount of flavoring and diluting agent within the capsule object 10 may vary. In some instances, the diluting agent may be eliminated altogether, and the entire inner payload 14 can be composed of the flavoring agent entirely. Alternatively, the inner payload 14 can be almost entirely comprised of diluting agent, and only contain a very small amount of relatively potent flavoring agent. In one embodiment, the composition of the mixture of flavoring and diluting agent is in the range of about 5 percent to about 75 percent flavoring, and more preferably in the range of about 5 to about 25 percent flavoring, and most preferably in the range of about 10 to about 15 percent, by weight based on the total weight of the inner payload 14, with the balance being diluting agent.

Preferably, the capsules 10 do not incorporate any tobacco within their outer shells 12, or within the inner payload 14. However, if desired, other aspects of capsules 10 may incorporate tobacco (e.g., as finely group tobacco pieces and/or tobacco extracts) within the outer shells 12 and/or within the inner payload 14 regions. Preferred components of the inner payload 14 provide a desired alteration to the sensory attributes of the tobacco product such as, for example, smell, flavor, and/or mouthfeel.

The size and weight of each capsule 10 may vary depending upon the desired properties it is to impart to the tobacco product. Preferred capsules 10 are generally spherical in shape. However, suitable capsules may have other types of shapes, such as generally rectilinear, oblong, elliptical, or oval shapes. Exemplary smaller spherical capsules have diameters of at least about 0.5 mm, generally at least about 1 mm, often at least about 2 mm, and frequently at least about 3 mm Exemplary larger spherical capsules have diameters of less than about 6 mm, and often less than about 5 mm Exemplary smaller individual capsules weigh at least about 5 mg, often at least about 10 mg, and frequently at least about 15 mg. Exemplary larger individual capsules weigh less than about 75 mg, generally less than about 65 mg, and often less than about 55 mg. In a preferred embodiment, the capsules define a weight between about 20 grams and about 30 grams and a maximum dimension between about 3 mm and about 4 mm.

The crush strength of the capsule objects 10 is sufficient to allow for normal handling and storage without a significant degree of premature or undesirable breakage. In particular, the crush strength of the outer shell 12 of the capsule objects 10 is sufficient to allow for normal handling and storage without a significant degree of premature and/or undesirable breakage. The crush strength of the capsule objects 10 also is sufficiently low so as to allow the tobacco product user to readily break a capsule object 10 in a purposeful manner when using the particular tobacco product that employs the capsule objects 10. Providing capsule objects 10 that possess both suitable integrity and ability to rupture can be determined by experimentation, depending upon factors such as capsule size and type, and may be a matter of design choice. See, for example, U.S. Pat. No. 7,479,098 to Thomas et al., which is incorporated herein by reference in its entirety.

During the manufacture of a tobacco product that includes a capsule 10, it may be desirable to inspect the tobacco product that includes the capsule 10 before the packaging and transport of the tobacco product that includes the capsule 10 for sale. It may be desirable, however, to inspect the capsule object 10 at additional or alternative stages during the manufacture of the tobacco product. For example, it may be desirable to inspect the capsule object 10 prior to incorporating the capsule object 10 into the tobacco product. Additionally or alternatively, it may be desirable to inspect the capsule 10 upon completion of manufacturing the capsule 10. Accordingly, aspects of the present disclosure are directed to systems and methods for inspecting capsules 10. More particularly, the present disclosure is directed to inspection of capsules 10 and tools employed in analyzing the capsules 10 to determine whether the capsules 10 are defective.

Figure 2:
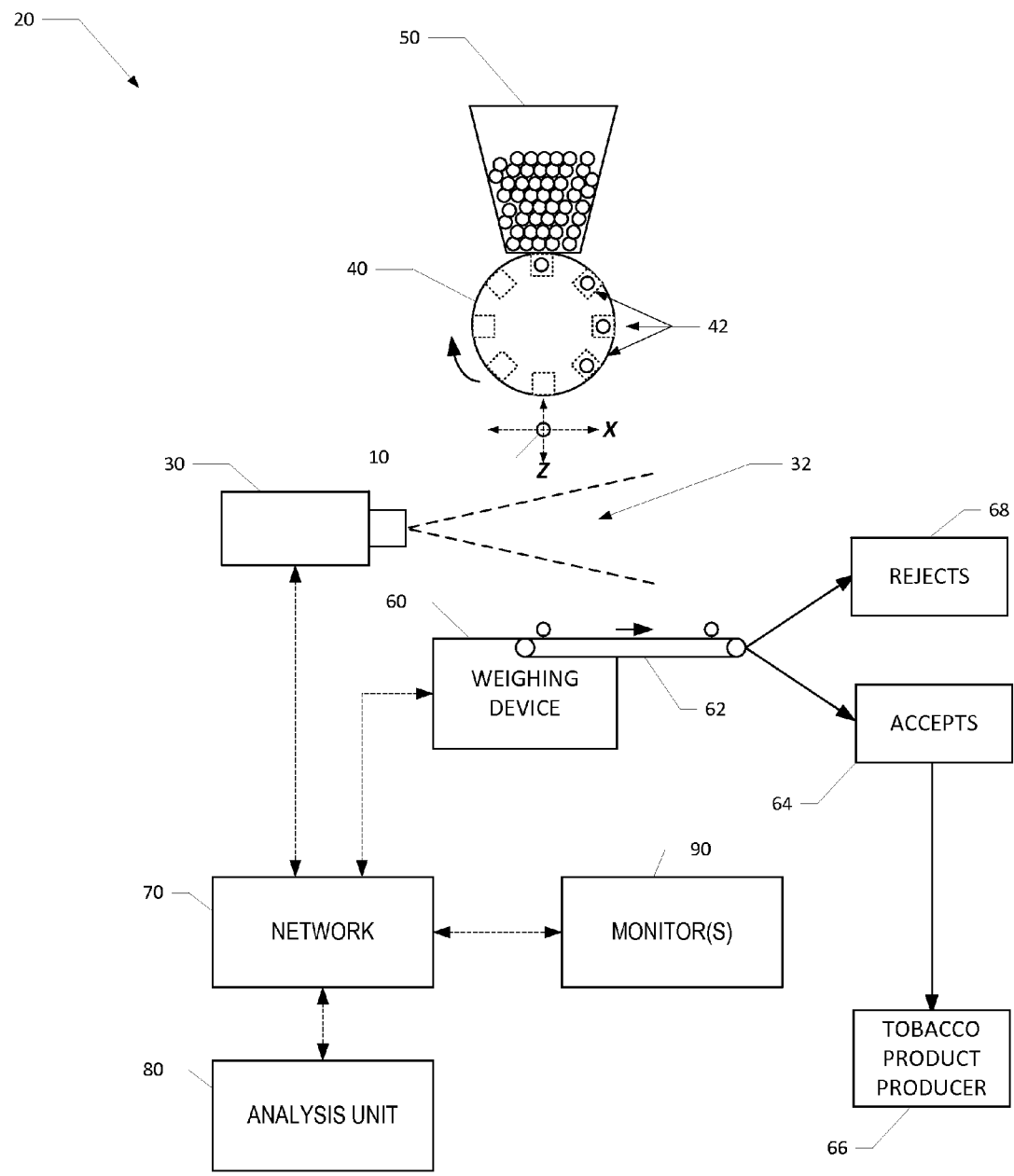
FIG. 2 illustrates a schematic view of a capsule object inspection system according to an example aspect of the present disclosure.

In this regard, FIG. 2 illustrates a schematic diagram of a capsule object inspection system 20 configured to inspect a capsule 10. As previously described, the capsule object 10 may comprise an outer shell 12 and an inner payload 14 (see, e.g., FIG. 1). The capsule object inspection system 20 may include at least one imaging device 30 and a weighing device 60. Further, the capsule object inspection system 20 may include an analysis unit 80. Accordingly, the analysis unit 80 may be configured to analyze data captured from the imaging device 30 and/or the weighing device 60. In some embodiments, the at least one imaging device 30 may be operably engaged with the analysis unit 80. According to additional embodiments, the at least one imaging device 30 may be configured to capture an image of the capsule 10 that may be outputted on a monitor (e.g., monitor 90), which may be connected to the at least one imaging device 30 and/or the analysis unit 80. According to some embodiments, the weighing device 60 may be operably engaged with the analysis unit 80. In some embodiments, a network 70 (e.g., a wired or wireless network) may be configured to transmit data between some or all of the components of the capsule object inspection system 20. For example, the network 70 may be configured to transmit data between the at least one imaging device 30 and the analysis unit 80 of the capsule object inspection system 20. Additionally or alternatively, the network 70 may be configured to transmit data between the weighing device 60 and the analysis unit 80.

According to some embodiments, the at least one imaging device 30 may include, by way of example, one or more infrared cameras, black and white cameras, color cameras, microwave devices, x-ray devices, magnetic resonance imaging (MRI) devices, thermal imaging devices, and/or any suitable visible spectrum imaging device. In one aspect, the at least one imaging device 30 includes an imaging device configured to capture one or more images of an exterior of the capsule object 10 (e.g., cameras configured to capture images in the visible light spectrum). As discussed hereinafter, the images of the exterior surface of the capsule object 10 may be taken from a frontal view. In particular, the imaging device 30 may be configured to capture images of the capsule 10 along a horizontal axis X of the capsule 10 and along a vertical axis Z of the capsule 10. Accordingly, the analysis unit 80 may be configured to analyze the images captured by the imaging device 30. Further, in some embodiments, the at least one imaging device 30 may include an illumination source (not shown) associated therewith, which may illuminate the exterior of the capsule object 10 in order to facilitate capturing images thereof.

In some embodiments, the at least one imaging device 30 may be configured to capture images in color. Further, the imaging device 30 may comprise high-speed cameras in some embodiments. For example, the imaging device 30 may be configured to capture at least about thirty frames per second in one embodiment, at least about fifty frames per second in an additional embodiment, and at least about sixty frames per second in a preferred embodiment. Accordingly, the imaging device 30 may be configured to capture images of the capsule object 10 while the capsule object moves at relatively high speeds (e.g., during the production thereof or during movements thereof prior to insertion into a tobacco product). In another embodiment, the imaging device 30 may be configured to capture images of the capsule object 10 while the capsule object moves at relatively high speeds as the capsule object is dispensed from a capsule dispensing device 40, discussed in further detail herein. Note that while inspection of the capsule objects 10 is preferably conducted during movement thereof, in other embodiments the capsules may be inspected while stationary or while moving at relatively lower speeds.

In one embodiment, the imaging device 30 may comprise the In-Sight 7000 Series Vision System, from Cognex Corp. of Natick, Mass. In this embodiment, the imaging device 30 may include integral illumination sources. Accordingly, a separate illumination source may be omitted in some embodiments.

According to one embodiment, the capsule inspection system 20 may further include a detection zone 32 that may be defined by the field of view of the at least one imaging device 30. As such, when a capsule object 10 passes through the detection zone 32, the at least one imaging device 30 may be configured to capture an image of the capsule objects 10 (e.g., of the exterior thereof). In another embodiment, the at least one imaging device 30 may be configured to capture images of the detection zone 32 at a predetermined interval. In some embodiments, the predetermined intervals may correspond with a particular timing interval where the capsule dispensing device 40 dispenses the capsule objects to the detection zone 32. In yet another embodiment, the capsule dispensing device 40 may be configured to dispense the capsule objects 10 directly to another inspection apparatus such as, for example, the weighing device 60.

In this regard, the capsule dispensing device 40 may include a rotatable wheel having a peripheral surface about the circumference of the capsule dispensing device 40 that defines a plurality of cavities 42. The capsule dispensing device 40 may be operably engaged with a capsule object repository 50. For example, the system 20 may include a capsule object repository 50 configured to handle and/or store a plurality of capsules 10 without any significant degree of premature and/or undesirable breakage of the outer shell 12 of the capsules 10. In some embodiments, the capsule object repository 50 may define an orifice that is in communication and operably engaged with the capsule dispensing device 40. In particular, the capsule object repository 50 may define an orifice that is in communication and operably engaged with the peripheral surface of the capsule dispensing device 40 that defines the plurality of cavities 42. In one aspect, gravity may urge the capsules 10 though the orifice defined by capsule object repository 50. Additionally or alternatively, the capsule object repository 50 may include a rotatable arm or other actuator within the interior volume of the capsule object repository 50 configured to urge the capsules 10 through the orifice.

Accordingly, when one of the cavities 42 of the capsule dispensing device 40 is aligned with the orifice defined by the capsule object repository 50, a capsule object 10 may be transported from the repository 50 to the cavity 42. According to some embodiments, the plurality of cavities 42 may be in fluid communication with a vacuum source configured to apply a suction force to each of the plurality of cavities 42. As such, when a cavity 42 aligns with the orifice of the capsule object repository 50, the suction force provided by the vacuum source may urge a capsule 10 from the repository 50 and into the cavity 42.

In some embodiments, the capsule dispensing device 40 may also be configured to eject a capsule object 10 from a particular cavity 42 when the particular cavity is positioned to dispense the capsule object 10 to the detection zone 32. In another embodiment, the capsule dispensing device 40 may be configured to eject a capsule object 10 from a particular cavity 42 when the particular cavity is positioned to dispense the capsule object 10 to another inspection apparatus such as, for example, the weighing device 60. For example, in some embodiments, the capsule dispensing device 40 may be configured such that when a cavity 42 is positioned to dispense a capsule 10 to the detection zone 32, the vacuum source that is operably engaged with and in fluid communication with the capsule dispensing device 40 no longer provides a suction force to the particular cavity 42 that is positioned to dispense the capsule 10. In another embodiment, the capsule dispensing device 40 may be configured such that when a cavity 42 is positioned to dispense a capsule 10 to the detection zone 32, a fluid source may be configured to provide a flow of a fluid (e.g., compressed air) to the cavity 42. In some embodiments, the injection of the compressed air into the cavity 42 may be configured to overcome the suction force that is provided by the vacuum source. In another embodiment, the vacuum source may no longer provide the suction force to the appropriately positioned cavity 42 and the injection of compressed air may be configured to urge the capsule 10 towards the detection zone 32.

As previously mentioned, the capsule dispensing device 40 may be configured to dispense and provide a capsule 10 to the detection zone 32 at a predetermined interval. For example, the plurality of cavities 42 defined by the capsule dispensing device 40 may be arranged along the peripheral circumference of the capsule dispensing device 40 at equal angular intervals. Accordingly, the rotational speed of the capsule dispensing device 40 may define the intervals between the introductions of each of the capsules 10 to the detection zone 32. For example, if the rotational speed of the capsule dispensing device 40 increases, the interval between the introductions of each of the capsules 10 decreases. Likewise, if the rotational speed of the capsule dispensing device 40 decreases, the interval between when each of the capsules 10 are introduced to the detection zone will increase.

As previously mentioned and shown in FIG. 2, according to some embodiments, the inspection system 20 may also include the weighing device 60 configured to weigh the capsule objects 10. According to one embodiment, the weighing device 60 may be configured to receive a capsule object 10 after the capsule object 10 is dispensed from the capsule dispensing device 40. In this regard, the system 20 may be configured such that the weighing device 60 receives a capsule object 10 after the capsule object has passed through the detection zone 32. Further, the weighing device 60 may receive a capsule object 10 after the at least one imaging device 30 has captured at least one image of the capsule object 10. For example, the imaging device 30 may capture one or more images of each capsule object 10 during freefall from the capsule dispensing device 40, wherein such freefall delivers the capsule object 10 to the weighing device 60. Thereby, freefall of the capsule object 10 may be employed to transport the capsule object 10 to and through the detection zone 32 and to the weighing device 60. As mentioned previously, the analysis unit 80 may be configured to analyze data captured by the weighing device 60. For example, the analysis unit 80 may be configured to analyze a weight measurement of the capsule object 10 that is captured by the weighing device 60.

In some embodiments, the weighing device 60 may comprise the Sartorius Weigh Cell Model WZA215-LC, from Sartorius Weighing Technology GmbH of Goettingen, Germany. According to some embodiments, the weighing device 60 may be configured to receive a series of capsule objects 10 from the capsule dispensing device 40. In particular, as the dispensing device 40 rotates, the capsule objects 10 are sequentially dispensed from the cavities 42 when a respective one of the cavities 42 is positioned to provide the capsule object 10 to the detection zone 32 and/or the weighing device 60. As such, continued rotation of the dispensing device 40 provides a series of capsule objects 10 to the detection zone 32 and/or the weighing device 60.

In some embodiments, the weighing device 60 may be configured to recalibrate after measuring the weight of the capsule objects 10. In one embodiment, the weighing device 60 may be configured to recalibrate between weighing each of the capsule objects 10. For example, the weighing device 60 may be configured to measure the weight of a first capsule object 10. Additionally, the weighing device 60 may be configured to retain the first capsule object 10 therein after measuring the weight of the first capsule object 10. According to various embodiments, the weighing device 60 may recalibrate (e.g., tare) after measuring the weight of the first capsule object 10 and while the weighing device 60 retains the first capsule object 10 therein. The dispensing device 40 may subsequently dispense a second capsule object 10 from a cavity 42 to the detection zone 32 and/or the weighing device 60. In some embodiments, the weighing device 60 may then obtain the weight of the second, subsequent capsule object 10 upon and/or after receiving the capsule object 10. Accordingly, by accounting for the weight of each capsule object 10 previously received and presently retained therein, the weighing device 60 may determine the weight of each individual capsule object 10.

According to another embodiment, as illustrated in FIG. 2, the weighing device 60 may include a transporting element 62 configured to remove the capsule object 10 from the weighing device after measuring the weight of the capsule object 10. In this regard, the transporting element 62 may be configured to divert a capsule object 10 to a storage unit for further processing after the weighing device 60 has obtained the weight of the capsule object 10. Accordingly, in some embodiments, the weighing device 60 may be configured to receive, retain, and/or measure a single capsule object 10 at a time. For example, a weighing device 60 may receive a first capsule object 10 in a series of capsule objects from the dispensing device 40. After the weighing device 60 measures the weight of the first capsule object 10, the transporting element 62 may remove the first capsule object 10 from the weighing device 60 before the weighing device 60 receives the second capsule object 10. In another embodiment, the transporting element 62 may remove the first capsule object 10 from the weighing device 60 before the dispensing device 40 provides the second capsule object 10 to the detection zone 32 and/or the weighing device 60.

In some embodiments, as illustrated in FIG. 2, the transporting element 62 may be configured to direct a capsule object 10 from the weighing device 60 to one of two flow paths based on a status of the capsule object as determined by the analysis unit 80. For example, when the analysis unit 80 determines that the capsule object 10 defines an accepted status (e.g., as a result of defining a weight as measured by the weighing device 60 that falls within a pre-specified weight interval and/or a shape, size, or other characteristic meeting specifications based on one or more images captured by the imaging device 30), the transporting element 62 may be configured to direct the capsule object 10 to a first storage unit 64 prior to transporting the accepted capsule object to a tobacco product producer 66 (e.g., a filter rod maker). Alternatively, the capsule objects defining the accepted status 80 may be directly transported to the tobacco product producer 66.

Additionally, when the analysis unit 80 determines that the capsule object 10 defines an unaccepted status (e.g., as a result of defining a weight as measured by the weighing device 60 that falls outside of a pre-specified weight interval and/or a shape, size, or other characteristic failing to meet specifications based on one or more images captured by the imaging device 30), the transporting element 62 may be configured to direct the capsule object to a second storage unit 64 prior to further analysis thereof, or disposal. As such, the transporting unit 62 may be configured to separate accepted (i.e., non-defective) and unaccepted (i.e., defective) capsule objects 10 such that only the accepted capsule objects are employed in production of tobacco products. According to some embodiments, the inspection system 20 may include a separate transporting unit configured to separate accepted and unaccepted capsule objects 10. For example, the inspection system 20 may include a transporting unit that is configured to direct the capsule objects 10 after at least one imaging device 30 captures an image of the exterior of the capsule objects 10 and an analysis unit 80 determines whether a particular capsule object 10 defines an accepted status (e.g., as a result of determining a dimension of the capsule object 10 based on one or more images captured by the imaging device 30). One example of an apparatus configured to sorting objects based on an accepted and/or rejected status is described in U.S. Pat. No. 8,905,243 to Dixon et al., which is incorporated herein by reference in its entirety.

Figure 3A:
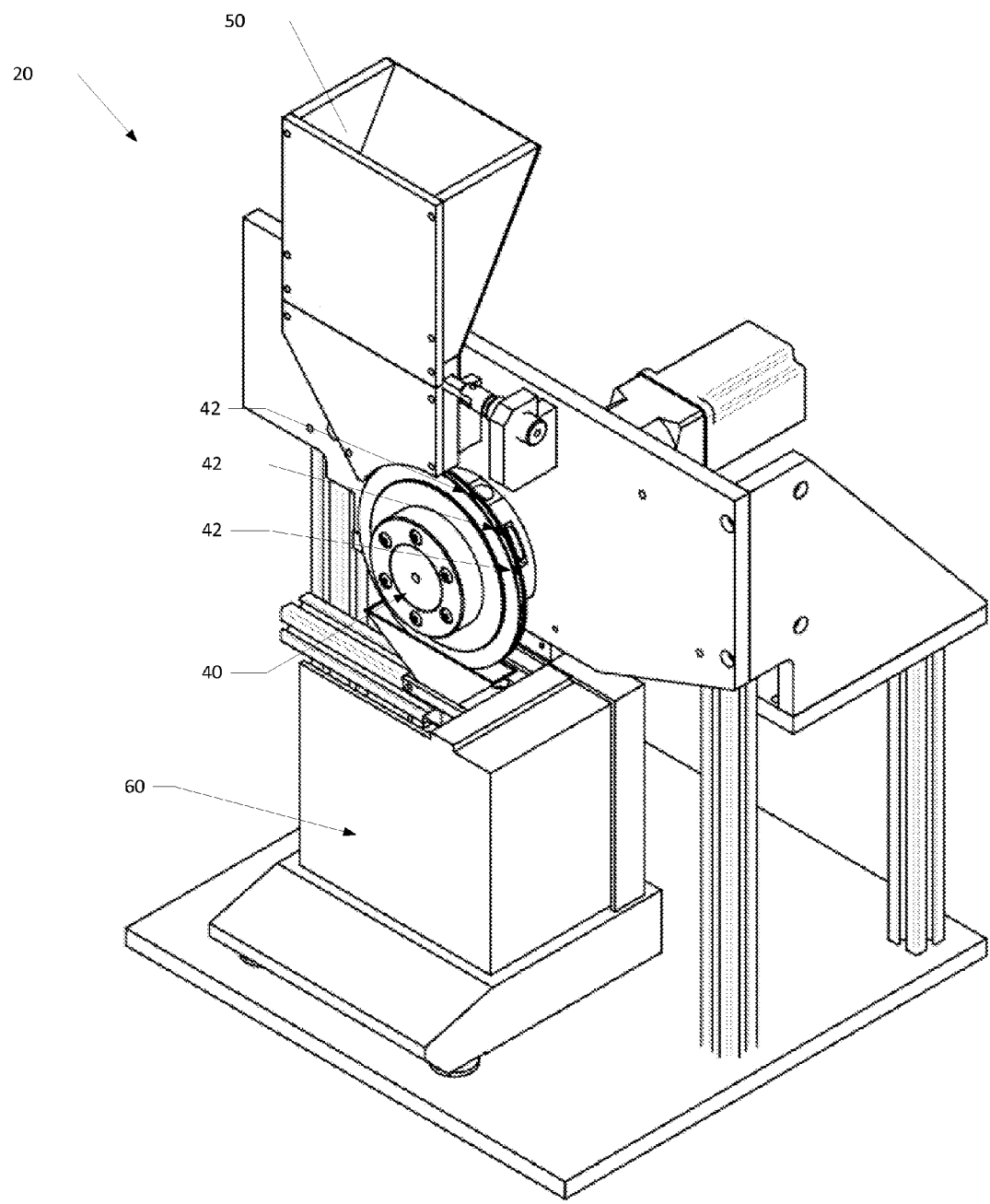
FIG. 3A illustrates a perspective view of a capsule object inspection system including a weighing device according to one example aspect of the present disclosure.
Figure 3B:
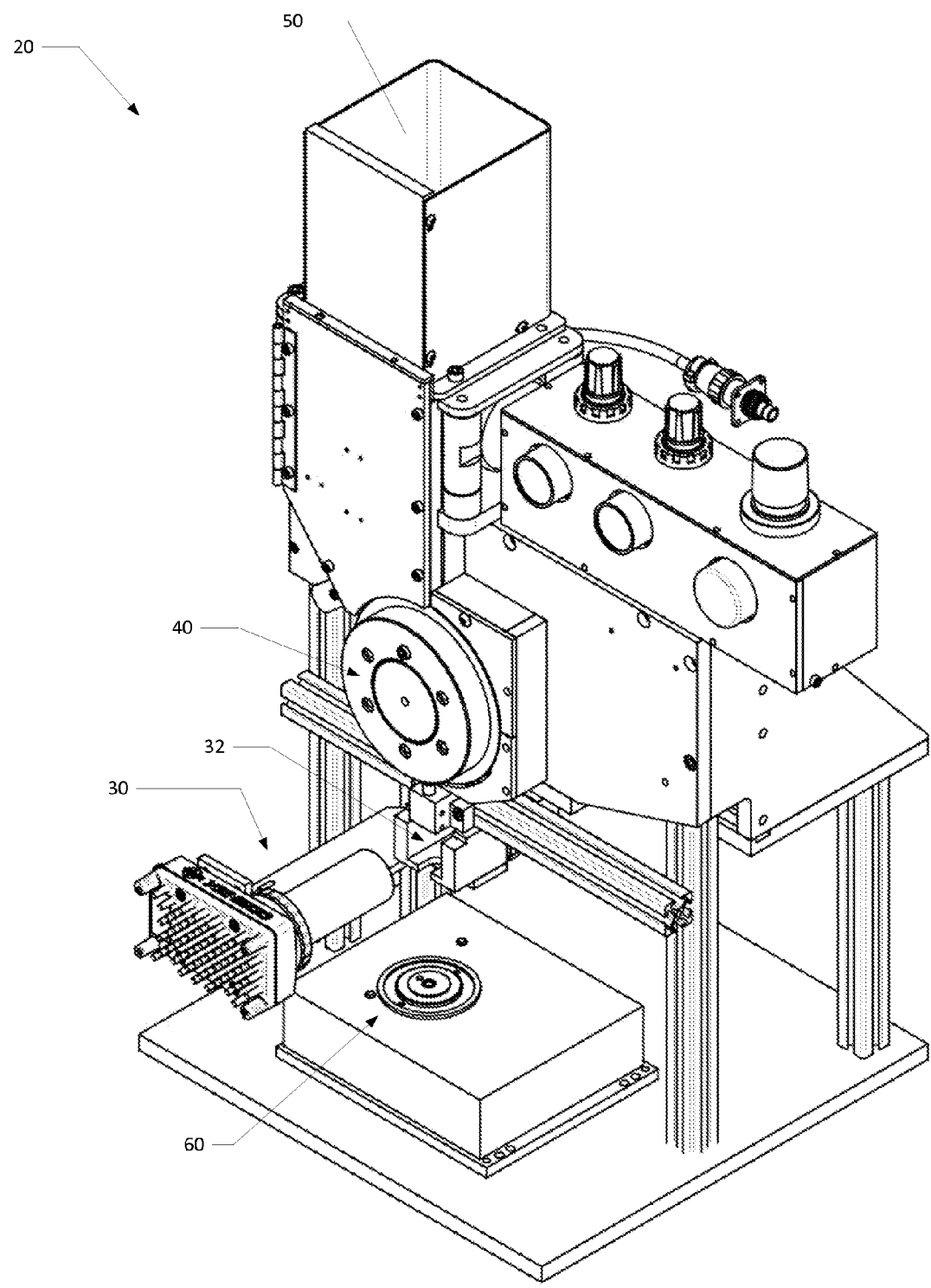
FIG. 3B illustrates a perspective view of a capsule object inspection system that includes a weighing device and an imaging device according to an additional example aspect of the present disclosure.

According to some embodiments, the capsule object inspection system 20 may be a modular system configured to determine whether a capsule object 10 is defective based on particular measurements, attributes, and/or properties of the capsule object 10. In this regard, FIGS. 3A and 3B illustrate perspective views of embodiments of the inspection system 20. As shown in FIG. 3A, according to one embodiment, the inspection system 20 may include the weighing device 60. Thereby, the inspection system 20 may be configured to determine if a capsule object 10 is defective by weighing each of the plurality of capsule objects 10.

In another embodiment, the inspection system 20, which is not separately illustrated herein, may be configured to determine whether any of a plurality of capsule objects 10 are defective based solely on a dimension of the capsule objects 10 determined from at least one image of the capsule objects 10 that is captured by at least one imaging device 30. In other words, in another embodiment, the system may include the imaging device 30, but not the weighing device 60.

Although some embodiments of the inspection system 20 are configured to determine whether a capsule object 10 is defective based on a single property and/or attribute of the capsule object 10, some embodiments of the inspection system 20 may be configured to determine whether a capsule object 10 is defective by ascertaining multiple properties and/or attributes of the capsule object 10. For example, as illustrated in FIG. 3B, in some embodiments, the inspection system 20 may include the at least one imaging device 30 configured to capture at least one image of the exterior of each of the plurality of capsule objects 10 and the weighing device 60 configured to measure the weight of each of the plurality of capsule objects 10. The at least one imaging device 30 may be configured to capture at least one image of the exterior of each of the capsule objects 10. As previously mentioned, the field of view of the at least one imaging device 30 may define a detection zone 32. The capsule dispensing device 40 may be operably engaged with a capsule repository 50 and may be configured to receive a plurality of capsule objects 10 from the capsule repository 50. Additionally, the capsule dispensing device 40 may be configured to transport capsule objects 10 from the capsule repository 50 to the detection zone 32 where at least one imaging device 30 is configured to capture at least one image of the exterior of the each of the capsule objects 10.

Accordingly, the components of the system 20 may be provided in any combination to analyze one or more aspects, features, properties, and/or the like of the plurality of capsule objects 10. In this regard, the inspection system 20 may be a modular system configured to determine whether a capsule object 10 is defective based on any of various measurements provided by one or more of various inspection apparatuses included therein. Note that while the inspection system 20 illustrated in FIG. 2 is preferably configured to determine a dimension of the capsule objects 10 and a weight of the capsule objects 10, in other embodiments, the inspection system 20 may be configured to determine additional and/or alternative properties of the capsule objects 10.

Figure 4:
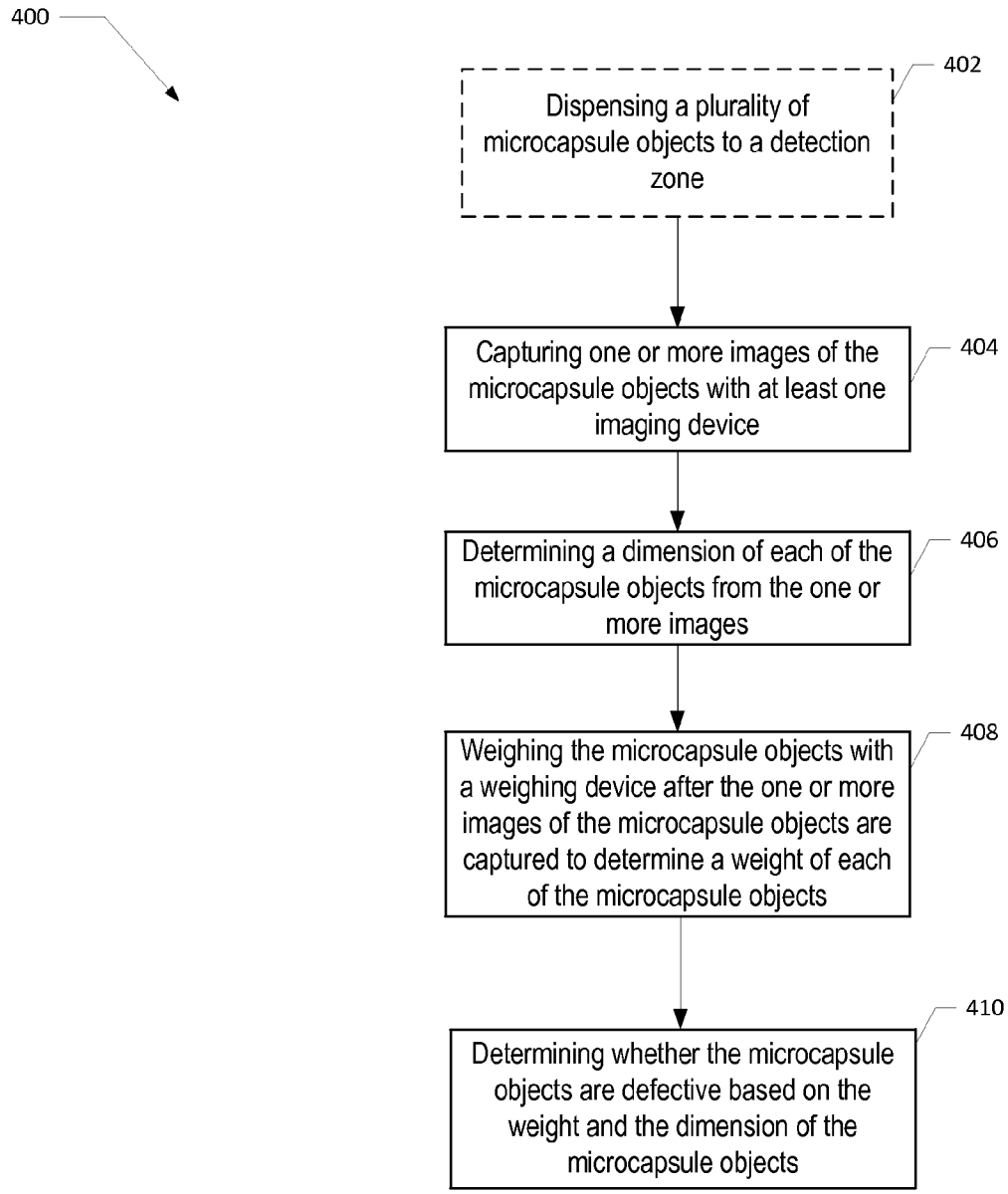
FIG. 4 illustrates a schematic block diagram of a method for inspecting a capsule object according to an example aspect of the present disclosure.

Various embodiments of the present disclosure may also provide a method of inspecting a capsule object that may be made or derived from tobacco, or otherwise incorporate tobacco, and may be intended for human consumption. For example, FIG. 4 illustrates such a method 400 for inspecting a capsule 10 that includes an outer shell 12 and an inner payload 14 (see, e.g., FIG. 1). According to one aspect, the method 400 may include dispensing a plurality of capsule objects to a detection zone (Block 402).

In this regard, a rotatable capsule dispensing device may have a peripheral circumferential surface that defines a plurality of cavities configured to receive and/or retain a capsule object therein. According to some aspects, the method may further include providing one of a plurality of capsule objects to each of the plurality of cavities defined by a peripheral circumferential surface of the dispensing device. The capsule dispensing device may rotate and dispense a capsule object to the detection zone that is defined by the field of view of the imaging device.

In some aspects, the method 400 may include capturing one or more images of the capsule objects with the at least one imaging device (Block 404). In particular, the method 400 may include capturing one or more images of the capsule objects with at least one imaging device. For example, the method 400 may include capturing one or more images of the exterior of the capsule objects with the at least one imaging device. As previously mentioned, the field of view of the imaging device may define a detection zone, and the method may include capturing one or more images of the capsule objects by the imaging device when the capsule objects traverse through the detection zone.

According to various aspects, the method 400 may include determining a dimension or other measure of each of the capsule objects from the one or more images captured by the at least one imaging device (Block 406). In this regard, the method 400 may include determining a dimension or other measure of each of the capsule objects with an edge detection tool. As previously mentioned, the imaging device may be operably engaged with an analysis unit configured to execute an edge detection tool. The edge detection tool may determine a dimension of each of the capsule objects based on the images of the capsule objects captured by the at least one imaging device. In particular, the edge detection tool may be configured to determine a dimension or other measure of size of the capsule objects from the image. In some embodiments, the edge detection tool may determine a dimension of the capsule object along the horizontal and/or vertical axis of the capsule object from the image. For example, the edge detection tool may determine a width of the capsule object along the horizontal axis of the capsule object from the at least one image and/or determine a height of the capsule object along the vertical axis of the capsule object from the at least one image. The edge detection tool may also be configured to determine a shape of the capsule object.

Some embodiments may provide for a method 400 that may include weighing the capsule objects with a weighing device (Block 408). For example, the method 400 may include weighing the capsule objects with a weighing device after the one or more images of the capsule objects are captured to determine a weight of each of the capsule objects. In some embodiments, the method 400 may include weighing the capsule objects with a weighing device configured to receive a series of capsule objects after each of the capsule objects pass through a detection zone. Additionally, the method 400 may include recalibrating the weighing device in between measuring the weight of each of the capsule objects. For example, a weighing device may measure the weight of a first capsule object received and/or retained therein. The weighing device may recalibrate (e.g., tare) after measuring the weight of the first capsule. The method 400 may further include the weighing device receiving a second capsule object from the capsule dispensing device. Additionally or alternatively, the method 400 may include weighing the second capsule object.

In some aspects, the method 400 includes determining whether the capsule objects are defective (Block 410). In this regard, the method 400 may include determining whether the capsule objects are defective based on the weight and/or the dimension of the capsule objects. In one embodiment, the method 400 may include determining whether the capsule objects are defective with an analysis unit. For example, the method may include determining whether the capsule objects are defective with an edge detection tool. As previously mentioned, an imaging device capturing an image of the capsule objects may be operably engaged with an analysis unit configured to execute an edge detection tool. The edge detection tool may compare the dimension of the capsule objects taken along the vertical axis and/or the horizontal axis of the capsule object with a predetermined capsule object dimension interval. If any of the measured dimensions of the capsule objects are not equal to or within the predetermined capsule object dimension interval, an edge detection module may transmit a signal to a processor indicating the capsule object is defective. In some embodiments, the edge detection tool compares the measured dimensions of the capsule objects taken along the horizontal axis and/or the vertical axis of the capsule objects to one another. In particular, if the difference between the measured dimensions is not substantially zero and/or negligible, then the edge detection module may transmit a signal to a processor indicating the capsule object is defective. As may be understood, various other measurements of size and shape may be employed in other embodiments, particularly in embodiments in which the capsule objects are intended to define configurations other than spherical (e.g., cylindrical, oval-shaped, etc.).

Additionally or alternatively, the method 400 may include determining whether the capsule objects are defective after weighing the capsule objects with a weighing device. In particular, the method 400 may include determining whether capsule objects are defective with a weight analysis tool. A weighing device may be operably engaged with an analysis unit configured to execute a weight analysis tool. The weight analysis tool may compare a measured weight of the capsule object with a predetermined capsule object weight interval. If the measured weight is not equal to or within the predetermined capsule object weight interval, the weight analysis module may transmit a signal to a processor indicating the capsule object is defective.

In some embodiments, the method 400 may further include discarding a capsule object if the capsule object is determined to be defective. In particular, the method 400 may include discarding a defective capsule object if an analysis unit determines the capsule object is defective. For example, a weighing device may include a transporting element. In some embodiments, the transporting element removes each capsule object from the weighing device after the weighing device measures the weight of each capsule object. According to some aspects, the method may include diverting a capsule object to a storage unit with a transporting element. For example, the transporting element may divert the capsule object to a storage unit after the weighing device measures the weight of the capsule object. In some embodiments, the transporting element may divert the capsule object to a first or second storage unit after the weighing device measures the weight of the capsule object. Additionally, the transporting element may direct capsule objects that are deemed accepted by an analysis unit to a first storage unit (i.e., accepted capsule storage unit), and may be further configured to direct capsule objects that are determined to be defective by an analysis unit to a second storage unit (i.e., defective capsule storage unit). For example, the transporting element may be configured to direct a capsule object that has a width along the capsule object's horizontal axis that differs from a height along the capsule object's vertical axis to the second storage unit. Additionally or alternatively, the transporting element may be configured to direct a capsule object having a measured weight that is not equal to or within a predetermined capsule object weight interval to the second storage unit. Likewise, in some embodiments, the transporting element may be configured to direct a capsule object having a dimension (e.g., width) along the capsule object's horizontal axis that is substantially equal to the dimension (e.g., height) along the vertical axis of the capsule object, or other measurements falling within predetermined limits, to the first storage unit. Additionally or alternatively, a transporting element may be configured to direct a capsule object having a weight equal to or within the predetermined capsule object weight interval to the first storage unit.

Figure 5:
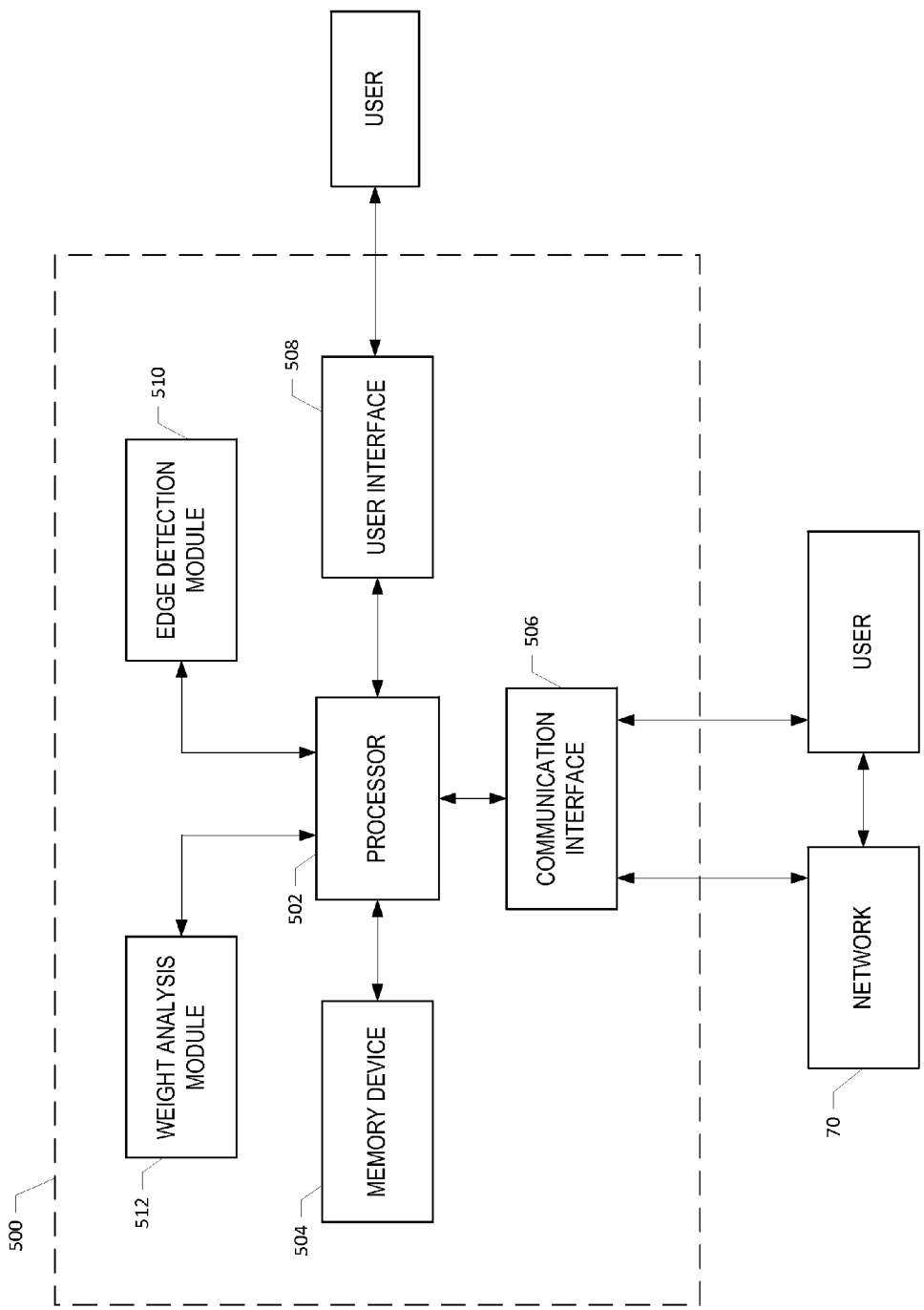
FIG. 5 illustrates a schematic view of components of an analysis unit of the capsule object inspection system of FIG. 2 according to one example aspect of the present disclosure.

Referring to FIG. 5, an apparatus 500 is provided that may be employed by devices performing functions in accordance with example aspects of the present disclosure. The apparatus 500 may be embodied, for example, as any device hosting, including, controlling, comprising, or otherwise forming a portion of the at least one imaging device 30, the analysis unit 80, the monitor(s) 90, and/or any other part of the capsule object inspection system 20 or the capsule object inspection system as a whole. According to one embodiment, the apparatus 500 may be embodied in or as the analysis unit 80. However, aspects of the apparatus 500 may also be embodied on a plurality of other devices such as, for example, where instances of the apparatus may be embodied on the network 70. As such, one aspect of the apparatus 500 is illustrated in FIG. 5 by way of example and may include more, or in some cases, less than the components shown in FIG. 5.

With further regard to FIG. 5, the apparatus 500 may be configured to analyze the image(s) captured by the at least one imaging device 30 and/or other data captured by the inspection system 20. As depicted in FIG. 5, the apparatus 500 may include or otherwise be in communication with a processor 502, a memory device 504, a communication interface 506, a user interface 508, an edge detection module 510, and/or a weight analysis module 512. The memory device 504 may include non-transitory and tangible memory that may be, for example, volatile and/or non-volatile memory. The memory device 504 may be configured to store information, data, files, applications, instructions or the like. For example, the memory device 504 could be configured to buffer input data for processing by the processor 502. Additionally or alternatively, the memory device 504 could be configured to store instructions for execution by the processor 502.

The apparatus 500 may, in some aspects, be a user terminal, a fixed communication device, and/or a computing device, such as a server configured to employ an example aspect of the present disclosure. However, according to some aspects, the apparatus 500 may be physically embodied as a chip or a chip set. The chip or chipset may constitute means for performing one or more operations for providing the functionalities described herein.

The processor 502 may be embodied in a number of different ways. For example, the processor 502 may be embodied as one or more of various processing means such as a coprocessor, a microprocessor, a controller, a digital signal processor (DSP), processing circuitry, or various other processing devices including integrated circuits such as, for example, a special-purpose computer chip, or other hardware processor. In an example aspect, the processor 502 may be configured to execute instructions stored in the memory device 504 or otherwise accessible to the processor. Additionally or alternatively, the processor 502 may be configured to execute hard coded functionality. As such, the processor 502 may be capable of performing operations according to aspects of the present disclosure while configured accordingly. Alternatively, when the processor 502 is embodied as an executor of software instructions, the instructions may specifically configure and/or cause the processor 502 to perform the operations described herein. The processor 502 may include a clock, an arithmetic logic unit (ALU), and/or logic gates that are configured to support operation of the processor 502, amongst other components.

The communication interface 506 may be any means such as a device or circuitry embodied in either hardware, software, or a combination thereof that is configured to receive and/or transmit data. In this regard, the communication interface 506 may include, for example, an antenna and supporting hardware and/or hardwired components and/or software. Accordingly, the communication interface 506 may provide for communication with external devices, such as the network 70, the at least one imaging device 30, the weighing device 60, and/or the monitor(s) 90. In some embodiments, the communication interface 506 may provide for communication with additional portions of the system 20, such as the capsule dispensing device 40. In some aspects, the communication interface 506 may provide for transmitting and/or receiving data through, for example, the wired or wireless network 70, such as a local area network (LAN), a metropolitan area network (MAN), and/or a wide area network (WAN), for example, the Internet.

In some embodiments, the apparatus 500 further includes a user interface 508. The user interface 508 may be in communication with the processor 502. For example, the user interface 508 may receive an indication of a user input at the user interface 508 and/or provide an audible/visible, mechanical (e.g., haptic), and/or other output to the user. As such, the user interface 508 may include, for example, a keyboard, a mouse, a joystick, a monitor or display, a touch screen, a microphone, a speaker, and/or any other suitable input/output mechanisms for performing the operations described herein. The processor 502 may be configured to control at least some functions of one or more elements of the user interface 508.

According to some aspects, the apparatus 500 may further include an edge detection module 510. The processor 502 may be configured to control at least some functions of one or more elements of the edge detection module 510. The edge detection module 510 may be configured to execute an edge detection tool configured to determine at least one exterior dimension of the capsule object 10 based on at least one image captured by the imaging device 30. Additionally or alternatively, the edge detection module 510 may be configured to execute an edge detection tool configured to determine if a capsule object 10 is defective based on the data provided by the at least one imaging device 30. In particular, the edge detection tool may be configured to determine whether a capsule object 10 is defective based on the at least one exterior dimension of the capsule 10 that was determined from an image captured by the at least one imaging device 30.

In this regard, the edge detection tool may be configured to determine an edge location of the capsule object 10 (i.e., an edge location of the outer shell 12). In particular, the edge detection tool may be configured to determine the location of the peripheral edge of the capsule object 10. For example, the imaging device 30 may capture a two-dimensional picture of the capsule object 10 taken along a frontal view, which illustrates the horizontal axis and the vertical axis of the capsule object 10. As such, the edge detection tool may be configured to determine the circumferential edge of the capsule object 10 within two dimensions (i.e., the two coordinate axis X and Z of the three possible coordinate axes in a traditional three-dimensional Cartesian coordinate system) from the image captured by the at least one imaging device 30, and may further be configured to capture images of the capsule objects in the third dimension in other embodiments, such that the thickness of the capsule objects may be determined According to one exemplary embodiment, the edge detection tool may be configured to determine a dimension of the capsule 10 from the image captured by the at least one imaging device 30, and more particularly, may be configured to determine a height of the capsule 10 along the vertical axis Z of the capsule object 10 and/or a width of the capsule 10 along the horizontal axis X of the capsule object 10.

As such, in one exemplary embodiment, the edge detection tool may be configured to compare the dimension of the capsule object 10 taken along the vertical axis Z (i.e., the height of the capsule object 10) and/or the dimension of the capsule object 10 taken along the horizontal axis X (i.e., the width of the capsule object 10) of the capsule object 10 with a predetermined capsule object dimension interval. The predetermined capsule object dimension interval may be associated with a dimension for an acceptable capsule object 10 suitable for incorporation within a tobacco and/or tobacco-related product. If the measured dimensions of the capsule object 10 are equal to or within the limits defining the predetermined capsule object dimension interval and/or other measures of the capsule object fall within pre-specified limits, the edge detection module 510 may be configured to provide a signal to the processor 502 indicating the capsule object 10 is suitable for incorporation within a tobacco and/or tobacco-related product. Additionally, if one or more of the measured dimensions of the capsule objects 10 are outside of the predetermined capsule object dimension interval and/or other measures of the capsule objects fall outside of the pre-specified limits, the edge detection module 510 may be configured to provide a signal to the processor 502 that the capsule object 10 is possibly defective and/or is not suitable for incorporation into a tobacco and/or tobacco-related product.

Additionally or alternatively, the edge detection tool may be configured to compare the dimension of the capsule object 10 taken along the vertical axis Z of the capsule with the dimension of the capsule object 10 that was taken along the horizontal axis X of the capsule object 10. Accordingly, the edge detection tool may be configured to determine whether a capsule object 10 is substantially spherical in three-dimensions and/or has a substantially circular profile in two-dimensions by comparing the measured dimensions that were determined for the horizontal axis X and the vertical axis Z of the capsule object 10. If the difference between the two measured dimensions of the capsule object 10 is negligible or substantially zero, then the edge detection module 510 may be configured to provide a signal to the processor 502 indicating the capsule object 10 is suitable for incorporation within a tobacco and/or tobacco-related product. Additionally, if the difference between the two measured dimensions of the capsule object 10 is greater than a pre-specified threshold, the edge detection module 510 may be configured to provide a signal to the processor 502 that the capsule object 10 is possibly defective and/or is not suitable for incorporation into a tobacco and/or tobacco-related product.

In another aspect, the apparatus 500 may further include a weight analysis module 512. The processor 502 may be configured to control at least some functions of one or more elements of the weight analysis module 512. The weight analysis module 512 may be configured to determine a weight of the capsule object 10. Additionally or alternatively, the weight analysis module 512 may be configured to execute a weight analysis tool configured to determine whether a capsule object 10 is defective based at least on the weight of the capsule object 10 previously measured by the weighing device 60.

The various features of the described aspects of the present disclosure can be used separately or in any combination. Various aspects described herein can be implemented by software, hardware or a combination of hardware and software. The described aspects can also be implemented as computer-readable program code portions on a computer readable storage medium for controlling and/or performing the above-described operations. In this regard, a computer readable storage medium, as used herein, refers to a non-transitory, physical storage medium (e.g., a volatile or non-volatile memory device), which can be read by a computer system. Examples of computer readable storage medium include read-only memory, random-access memory, CD-ROMs, DVDs, magnetic tape, optical data storage devices and/or the like. The computer readable storage medium can also be distributed over network-coupled computer systems so that the computer-readable program code portions are stored and executed in a distributed fashion.

As previously mentioned, the processor 502 may be configured to execute computer-readable program code portions for performing the above-described operations. In this regard, an aspect of a non-transitory computer readable storage medium that has computer-readable program code portions stored therein that, in response to execution by a processor (e.g., processor 502), causes an inspection system to inspect a capsule object having an outer shell and an inner payload is provided. The non-transitory computer readable storage medium may include computer-readable program code instructions that, when executed by a processor, cause a system to receive at least one image of one of a series of capsule objects. In particular, the non-transitory computer readable storage medium may include computer-readable program code instructions that, when executed by a processor, cause an imaging device to capture an image of each of a plurality of capsule objects in a detection zone, which may be defined by the field of view of the imaging device. Additionally, in some embodiments, the non-transitory computer readable storage medium may include computer-readable program code instructions that cause the imaging device to transmit data corresponding to the captured image of the capsule object to an analysis unit.

According to some aspects, the non-transitory computer-readable storage medium may include computer-readable program code portions that, when executed by a processor, cause the inspection system to determine a dimension of the capsule objects from the at least one image captured by the imaging device. In particular, the computer-readable program code portions, when executed by a processor, may cause an analysis unit to measure a dimension of the capsule object along the capsule object's horizontal axis and/or measure a dimension of the capsule object along the capsule object's vertical axis. In this regard, the computer-readable program code portions, when executed by a processor, may cause an analysis unit to measure the width of the capsule objects along the horizontal axis of the capsule objects and may cause an analysis unit to measure a height of the capsule objects along the vertical axis of the capsule objects from the at least one image of the capsule objects.

In another embodiment, the non-transitory computer-readable storage medium may include computer-readable program code portions, that when executed by a processor, cause the inspection system to receive a weight of the capsule object. In particular, according to one aspect, the non-transitory computer readable storage medium may include computer-readable program code instructions, that when executed by a processor, cause a weighing device to measure the weight of each of the capsule objects. In some embodiments, the computer-readable program code instructions, when executed by a processor, may cause the weighing device to measure the weight of one of each of the capsule objects that are received by the weighing device in substantially equal time intervals. According to some embodiments, the computer-readable program code instructions, when executed by a processor, may cause the weighing device to recalibrate between weighing each of the capsule objects.

According to some aspects, the non-transitory computer-readable storage medium may include computer-readable program code portions, that when executed by a processor, may cause an inspection system to determine whether each of the capsule objects are defective based on the at least one image and the weight of the capsule objects. For example, the computer-readable program code portions may include code portions, that when executed by a processor, cause an analysis unit to compare measured dimensions of a capsule object taken along a horizontal and/or vertical axis of the capsule object with an acceptable predetermined capsule object dimension interval. If the measured dimension(s) are outside the limits of the acceptable predetermined capsule object dimension interval, the computer-readable program code portions may include code portions, that when executed by a processor, cause a processor to indicate, determine, and/or otherwise signal that the capsule object is defective. Additionally or alternatively, the computer-readable program code portions may include code portions, that when executed by a processor, cause an analysis unit to compare a measured weight of a capsule with an acceptable predetermined capsule object weight interval. If the measured weight is outside the limits of acceptable predetermined capsule object weight interval, the computer-readable program code portions may include code portions, that when executed by a processor, cause a processor to indicate, determine, and/or otherwise signal that the capsule object is defective.

Many modifications and other aspects of the disclosure set forth herein will come to mind to one skilled in the art to which the disclosure pertains having the benefit of the teachings presented in the foregoing description and the associated drawings. Therefore, it is to be understood that the disclosure is not to be limited to the specific aspects disclosed and that modifications and other aspects are intended to be included within the scope of the appended claims. Moreover, although the foregoing description and the associated drawings describe example aspects in the context of certain example combinations of elements and/or functions, it should be appreciated that different combinations of elements and/or functions may be provided by alternative aspects without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An inspection system configured to inspect a plurality of capsule objects, each of the capsule objects comprising an outer shell and an inner payload, the inspection system comprising:

at least one imaging device configured to capture at least one image of an exterior of each of the capsule objects as each of the capsule objects is freefalling;

a weighing device configured to receive each of the freefallen capsule objects and to measure a weight of each of the capsule objects; and a capsule analyzer having a processor and being in communication with the at least one imaging device and the weighing device, the capsule analyzer being responsive to the at least one image of each of the capsule objects received from the at least one imaging device, and the corresponding weight of each of the capsule objects received from the weighing device, to determine whether each of the capsule objects is defective in comparison to a predetermined dimension and a predetermined weight of a non-defective capsule object.

2. The inspection system of claim 1 further comprising a capsule dispensing device comprising a peripheral surface, the peripheral surface defining a plurality of cavities configured to receive the capsule objects therein, and the capsule dispensing device configured to sequentially introduce the capsule objects to a detection zone, the detection zone being defined by a field of view of the at least one imaging device.

3. The inspection system of claim 2 further comprising a capsule object repository operably engaged with the capsule dispensing device, the capsule object repository configured to retain a plurality of capsule objects therein.

4. The inspection system of claim 1, wherein the weighing device is configured to measure the weight of a series of the capsule objects after the at least one imaging device has captured the at least one image of the exterior of at least one of the capsule objects.

5. The inspection system of claim 4, wherein the weighing device is configured to recalibrate between measuring the weight of each of the capsule objects.

6. The inspection system of claim 1, comprising an edge detection tool configured to determine a width of each of the capsule objects along a horizontal axis from the at least one image of the exterior of the capsule objects.

7. The inspection system of claim 6, wherein the edge detection tool is further configured to determine a height of the capsule objects along a vertical axis from the at least one image of the exterior of the capsule objects.

8. The inspection system of claim 1, comprising a weight analysis tool configured to compare the weight of each of the capsule objects with a predetermined capsule object weight interval.

9. A method for inspecting a plurality of capsule objects comprising an outer shell and an inner payload, the method comprising:

capturing one or more images of an exterior of each of the capsule objects with at least one imaging device as each of the capsule objects is freefalling;

measuring a weight of each of the freefallen capsule objects received by a weighing device;

determining whether each of the capsule objects is defective in comparison to a predetermined dimension and a predetermined weight of a non-defective capsule object in response to the one or more images of each of the capsule objects received from the at least one imaging device and the corresponding weight of each of the capsule objects received from the weighing device by a capsule analyzer having a processor and being in communication with the at least one imaging device and the weighing device.

10. The method of claim 9, comprising determining a width of the capsule objects along a horizontal axis of the capsule objects and a height of the capsule objects along a vertical axis of the capsule objects.

11. The method of claim 9 further comprising dispensing the capsule objects to a detection zone defined by a field of view of the at least one imaging device.

12. The method of claim 11 further comprising providing the capsule objects to a plurality of cavities defined by a peripheral surface of a dispensing device, the dispensing device configured to sequentially dispense one of the capsule objects to the detection zone.

13. The method of claim 11, further comprising dispensing the capsule objects to the weighing device.

14. The method of claim 13, wherein dispensing the capsule objects to the detection zone and dispensing the capsule objects to the weighing device comprise dropping the capsule objects from a dispensing device sequentially.

15. The method of claim 9 further comprising recalibrating the weighing device between weighing each of the capsule objects.

16. The method of claim 9, wherein determining whether the capsule object is defective comprises:

comparing the weight of the capsule objects with a predetermined capsule object weight interval; and comparing the dimension of capsule objects with a predetermined capsule object dimension interval.

17. The method of claim 16 further comprising discarding the capsule objects that are determined to be defective.

18. A computer-readable storage medium that is non-transitory and has computer-readable program code portions stored therein that, in response to execution by a processor, cause a system to at least:

capture at least one image of an exterior of each of a plurality of capsule objects with at least one imaging device as each of the capsule objects is freefalling;

measure a weight of each of the freefallen capsule objects received by a weighing device; and determine whether each of the capsule objects is defective in comparison to a predetermined dimension and a predetermined weight of a non-defective capsule object in response to the at least one image of each of the capsule objects received from the at least one imaging device, and the corresponding weight of each of the capsule objects received from the weighing device by a capsule analyzer having a processor and being in communication with the at least one imaging device and the weighing device.

19. The computer-readable storage medium of claim 18, further comprising computer-readable program code portions that cause the system to determine a width of each of the capsule objects along a horizontal axis of the capsule objects and a height of each of the capsule objects along a vertical axis of the capsule objects.

20. The computer-readable storage medium of claim 18 further comprising computer-readable program code portions that cause the system to recalibrate a weighing device between measuring a weight of each of the capsule objects.

* * * * *